United States Patent [19]
Prater et al.

[11] Patent Number: 5,322,067
[45] Date of Patent: Jun. 21, 1994

[54] METHOD AND APPARATUS FOR DETERMINING THE VOLUME OF A BODY CAVITY IN REAL TIME

[75] Inventors: David M. Prater, Cambridge; Christina Banta, Andover; Albert F. Koch, III, Newburyport, all of Mass.

[73] Assignee: Hewlett-Packard Company, Palo Alto, Calif.

[21] Appl. No.: 12,720

[22] Filed: Feb. 3, 1993

[51] Int. Cl.$^5$ ................................................ A61B 8/00
[52] U.S. Cl. .......................... 128/660.07; 128/661.10; 128/916
[58] Field of Search ...................... 128/660.07, 660.02, 128/660.06, 661.08, 661.10, 916

[56] References Cited

U.S. PATENT DOCUMENTS

| | | | |
|---|---|---|---|
| 4,867,167 | 9/1989 | Magnin | 128/660.06 |
| 5,097,836 | 3/1992 | Yamada et al. | 128/660.07 |
| 5,195,521 | 3/1993 | Melton, Jr. et al. | 128/660.02 |
| 5,211,169 | 5/1993 | Freeland | 128/661.08 |
| 5,224,483 | 7/1993 | Lipschutz | 128/662.02 |

Primary Examiner—William E. Kamm
Assistant Examiner—George Manuel

[57] ABSTRACT

A method and apparatus for determining the volume of a fluid-filled cavity in a patient's body in real time from an ultrasound image. An ultrasound display of the cavity and the surrounding tissue is obtained. The ultrasound display includes a sequence of ultrasound images. The user traces a fixed region of interest around the image of the cavity at the largest volume for which the volume determination is to be made. The region of interest is subdivided into a predetermined number of segments. Each pixel of the ultrasound image, at least within the region of interest, is classified as a fluid pixel or a tissue pixel. The area of fluid pixels within each segment is determined. The volume of the cavity is calculated from the area of the fluid pixels within each segment of the region of interest using the method of disks. The volume is determined for each ultrasound image in the sequence of ultrasound images to provide the volume of the cavity in real time.

14 Claims, 10 Drawing Sheets

METHOD AND APPARATUS FOR DETERMINING THE VOLUME OF A BODY CAVITY IN REAL TIME

FIELD OF THE INVENTION

This invention relates to techniques for determining the volume of a body cavity by ultrasonic imaging and, more particularly, to methods and apparatus for determining the volume of a blood-filled cavity, such as a ventricle of a heart, in real time.

BACKGROUND OF THE INVENTION

Information as to the volume of the left ventricle of the heart as a function of time is useful to a cardiologist in evaluating the heart. In particular, the volume at diastole, the volume at systole, the rate of change of volume and other parameters based on volume provide useful information to the cardiologist.

One approach to determining the volume of the left ventricle of the heart is by ultrasound imaging. The volume is determined from a two-dimensional ultrasound image by determining the cross-sectional area from the ultrasound image and making certain assumptions regarding the shape of the left ventricle.

In one approach, a user selects a still frame apical 4 chamber or apical 2 chamber ultrasound image and manually traces the outline of the ventricle as it appears on the image using a trackball or similar device. In addition, the user selects a long axis which serves as an axis of rotation. The volume is determined by rotating the two-dimensional traced area about the selected axis to provide a circularly symmetric volume. The volume is computed using a technique known as method of disks. After the user has precisely traced the border between the ventricle and the endocardium, the traced region is segmented into a number of parallel slices. The volume of each of the slices is computed. The volumes are summed to provide the volume of the entire ventricle. The segmentation is based on the traced region. In order to determine the volume in another frame, the user precisely traces the ventricle and the volume is calculated in the same way. The segmentation is based on the traced area, which varies from frame to frame. This technique provides the volume one frame at a time and is typically performed only at diastole and systole.

Another technique for determining the volume of a ventricle is described in application Ser. No. 07/614,780, filed Nov. 9, 1990, assigned to the assignee of the present application. Signals from an ultrasound scanner are processed to determine whether they represent blood or tissue. Incremental areas of the image which represent blood and which fall within a region of interest having a truncated annular shape are rotated about the long axis of the ventricle to form an incremental volume of revolution. The total volume of the ventricle is derived by summing the incremental volumes.

In another prior art system, a region of interest is traced by a user on an ultrasound image. Signals from the ultrasound scanner are processed to determine whether they represent blood or tissue. Blood areas within the region of interest are summed in an accumulator to determine the total blood area within the region of interest. The volume is not determined.

All of the prior art techniques for determining ventricular volume have had various disadvantages, including inability to determine volume in real time, excess complexity and the like.

SUMMARY OF THE INVENTION

According to the present invention, methods and apparatus for determining the volume of a fluid-filled cavity in a patient's body in real time are provided. Typically, the invention is utilized to determine the volume of a blood-filled cavity, such as the left ventricle of the heart. As used herein, the term "pixel" refers to an incremental area of a sector scan ultrasound image corresponding to one sample of the received ultrasound signal. Each pixel in the sector scan ultrasound image has a truncated annular shape. The areas of the pixels increase with distance from the apex of the sector scan.

The method in accordance with the invention comprises the steps of (a) obtaining a real time, two-dimensional ultrasound display of the cavity and the surrounding tissue, the ultrasound display comprising a sequence of ultrasound images, (b) determining parameters of a fixed, user-defined region of interest surrounding the ultrasound display of the cavity at the largest volume for which a volume calculation is to be made, (c) subdividing the region of interest into a predetermined number of segments, (d) classifying each pixel, at least within the region of interest, of an ultrasound image in the sequence of ultrasound images as a fluid pixel which represents fluid or a tissue pixel which represents tissue, (e) determining the area of fluid pixels within each segment, (f) calculating the volume of the cavity from the area of fluid pixels within each segment of the region of interest, and (g) repeating steps (d) through (f) for each ultrasound image of the sequence of ultrasound images to provide the volume of the cavity at each of the times when the ultrasound images were obtained. The present invention permits the volume of the cavity to be determined on multiple ultrasound images with a single region of interest, thereby reducing the calculation time and permitting the determination of volume in real time for each ultrasound image in the sequence of ultrasound images.

The step of calculating the volume of the cavity preferably includes the steps of approximating a volume of the cavity within each segment by a disk having a height equal to the height of the segment and a diameter equal to the total area of the fluid pixels divided by the height, calculating the volume of the disk in each segment of the region of interest, and summing the volumes of the disks in the segments in the region of interest to provide the volume of the cavity.

The parameters of the region of interest are defined by determining the coordinates of a boundary of a region of interest traced by the user, determining a long axis of the region of interest and determining an angle between the normal to the long axis and the horizontal axis of the display screen. The region of interest is preferably subdivided by spaced lines normal to the long axis of the region of interest.

The step of determining the area of fluid pixels within each segment of the region of interest preferably includes the steps of storing a start depth, a stop depth and a segment number for each segment along each scan line, and storing the area of fluid pixels within each segment in an accumulator corresponding to the segment number when a depth between the start depth and the stop depth of the corresponding segment along each scan line is being scanned.

BRIEF DESCRIPTION OF THE DRAWINGS

For a better understanding of the present invention, reference is made to the accompanying drawings, which are incorporated herein by reference and in which.

DETAILED DESCRIPTION

The present invention provides methods and apparatus for determining the volume of a fluid-filled cavity, such as the left ventricle of the heart, in a patient's body in real time using an ultrasound imaging system. An ultrasound image of the cavity to be measured is displayed on a video display screen. A user traces a fixed region of interest around the cavity. The region of interest is large enough to enclose the cavity at its largest volume. The region of interest is divided into segments. The fluid area within each segment of the region of interest is determined by signal processing of the signals used to generate the ultrasound image. The volume of the cavity within each segment of the region of interest is approximated by a disk. The volume of the disk within each segment is calculated, and the volumes of the disks are summed to provide the total volume of the cavity. The process is repeated for each image, or frame, of the ultrasound display, with the region of interest remaining fixed, to provide a measurement of the cavity volume as a function of time.

Figure 1:
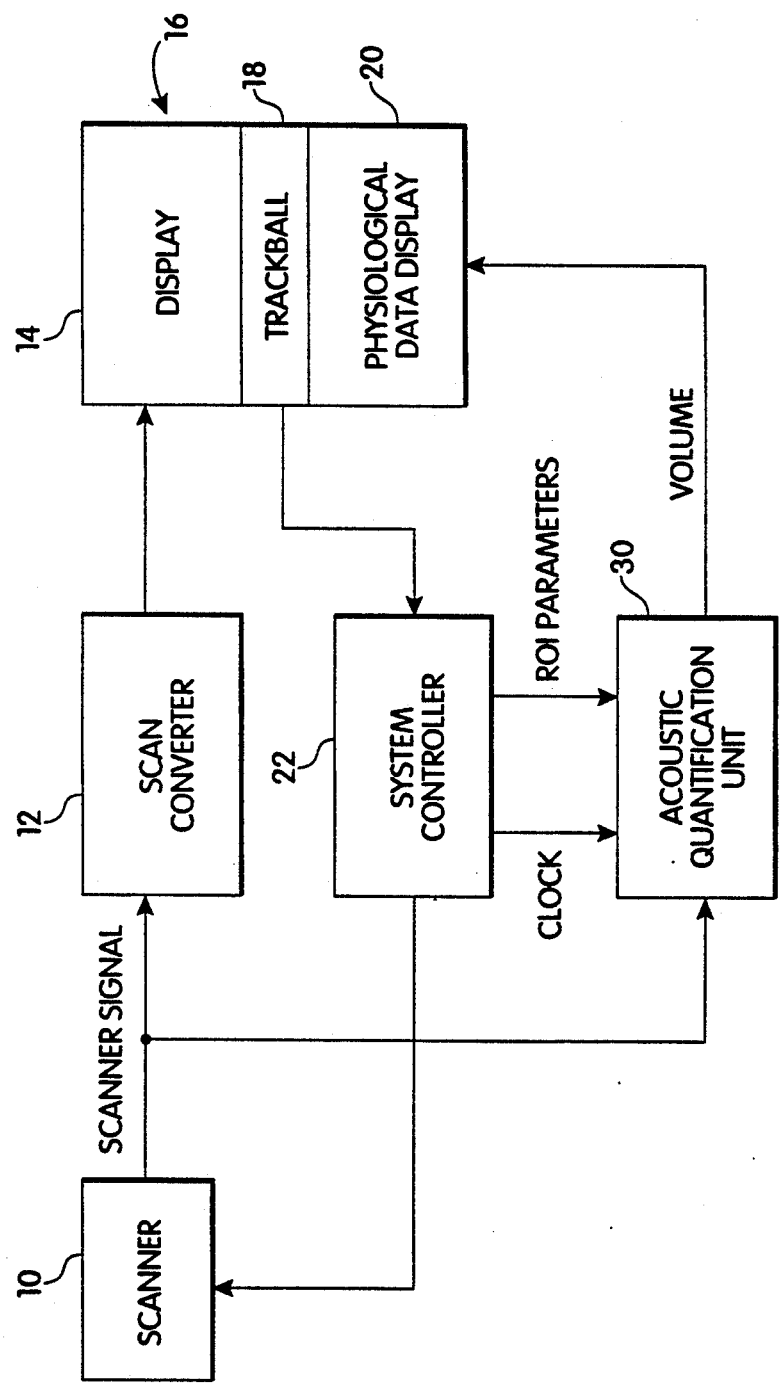
FIG. 1 is a block diagram of an ultrasound imaging system including an acoustic quantification unit for determining the volume of a fluid-filled cavity in accordance with the present invention.

A simplified block diagram of a system for determining volume in accordance with the present invention is shown in FIG. 1. A scanner 10 performs ultrasound scanning of a specified region of a patient's body, such as the heart. The scanner includes an ultrasound transducer for transmitting and receiving ultrasound energy. The transducer transmits ultrasound energy into a region being imaged and receives reflected ultrasound energy from various structures and organs within the patient's body.

The transducer may include an array of transducer elements. As is known in the prior art, by appropriately delaying the pulses applied to each transducer element, a focused ultrasound beam is transmitted along a desired scan line. The reflected ultrasound energy from a given point within the patient's body is received by the transducer elements at different times. The transducer elements convert the received ultrasound energy to electrical signals which are supplied to a receive beamformer. The beamformer processes the electrical signals to effect focusing and steering of the received ultrasound energy. The beamformer converts the received ultrasound energy into a focused received beam. The depth and direction of the focal point relative to the ultrasound transducer can be varied dynamically with time by appropriately delaying the received signals from each of the transducer elements. The delayed signals from each transducer element are summed to provide a scanner signal that is a representation of the reflected energy level along a given scan line. The process is repeated for multiple scan lines to provide signals for generating an image of the prescribed region of the patient's body. Typically, the scan pattern is a sector scan wherein the scan lines originate at a point at the center of the ultrasound transducer and are directed at different angles.

Alternatively, the scanner 10 can include a mechanical scanner for ultrasound scanning of a specified region of the patient's body. In a mechanical scanner, an ultrasound transducer is scanned across the specified region by a motor. Mechanical scanners are well known to those skilled in the art.

The scanner signal is applied to a scan converter 12, of a type known in the art, which converts the sector scan information generated by scanner 10 to a conventional raster scan display signal. The output of scan converter 12 is applied to a display 14 such as a video display unit. The display 14 is part of an operator interface 16. The operator interface 16 may also include a trackball 18 for tracing a region of interest as described below and a physiological data display 20. The physiological data display 20 may, for example, include an alphanumeric display for display of physiological data and a video display unit or a chart recorder for display of physiological waveforms. As described below, the physiological data display 20 can be used to display the volume of a fluid-filled cavity in the patient's body as a function of time. The operator interface 16 may also include operator control such as a keyboard and/or dedicated function keys (not shown) for setup, adjustment and control of the system.

A system controller 22 provides overall control of the system. The system controller 22 performs timing and control functions and may include a microprocessor and associated memory. As described below, the system controller 22 determines region of interest parameters based on a region of interest traced by a user using trackball 18.

The system shown in FIG. 1 further includes an acoustic quantification unit 30 for determining the volume of a fluid-filled cavity in the ultrasound display. The volume is determined in real time on an image-by-image basis from the scanner signal that is used to generate the ultrasound display and the region of interest parameters supplied by the system controller 22. The volume determined by the acoustic quantification unit 30 is output to the physiological data display 20 of operator interface 16. The volume information can also be recorded by a printer, a chart recorder or a magnetic storage device, or can be transmitted on a network to a computer or other instrumentation.

Figure 2B:
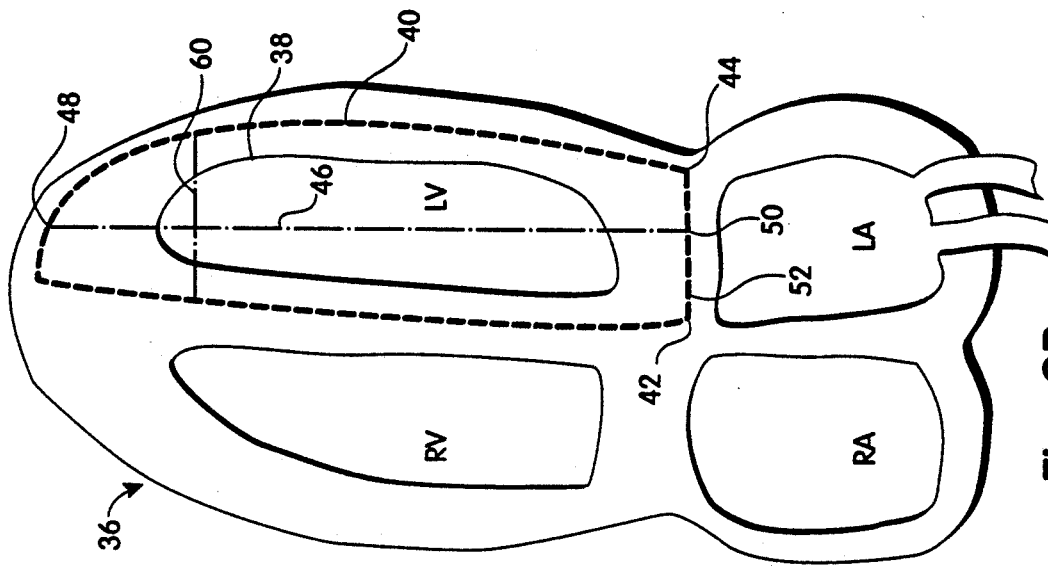
FIGS. 2A and 2B show a fixed region of interest superimposed on an ultrasound image of a left ventricle at diastole and systole, respectively.
Figure 2A:
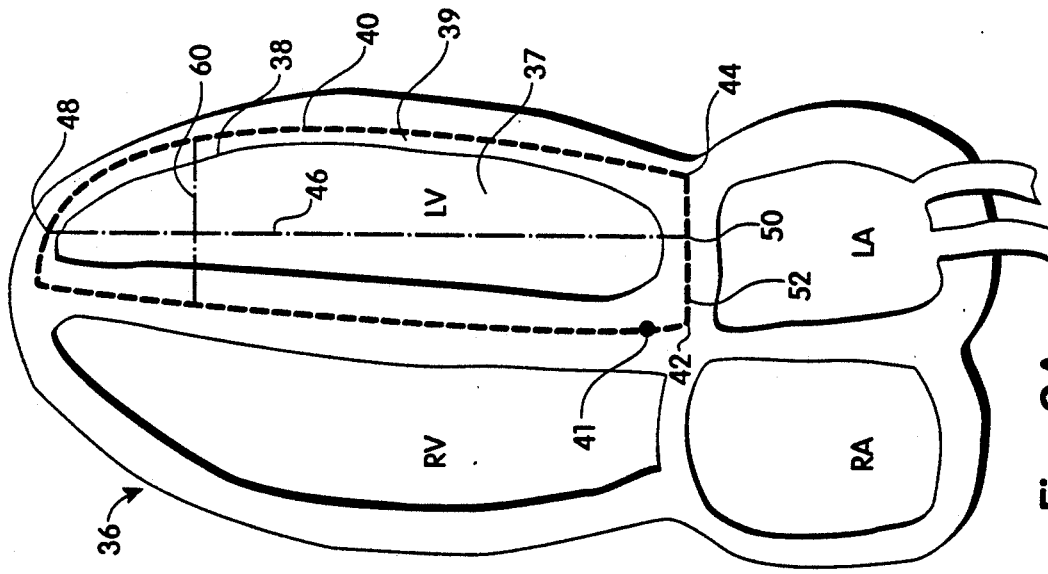
Figure 3:
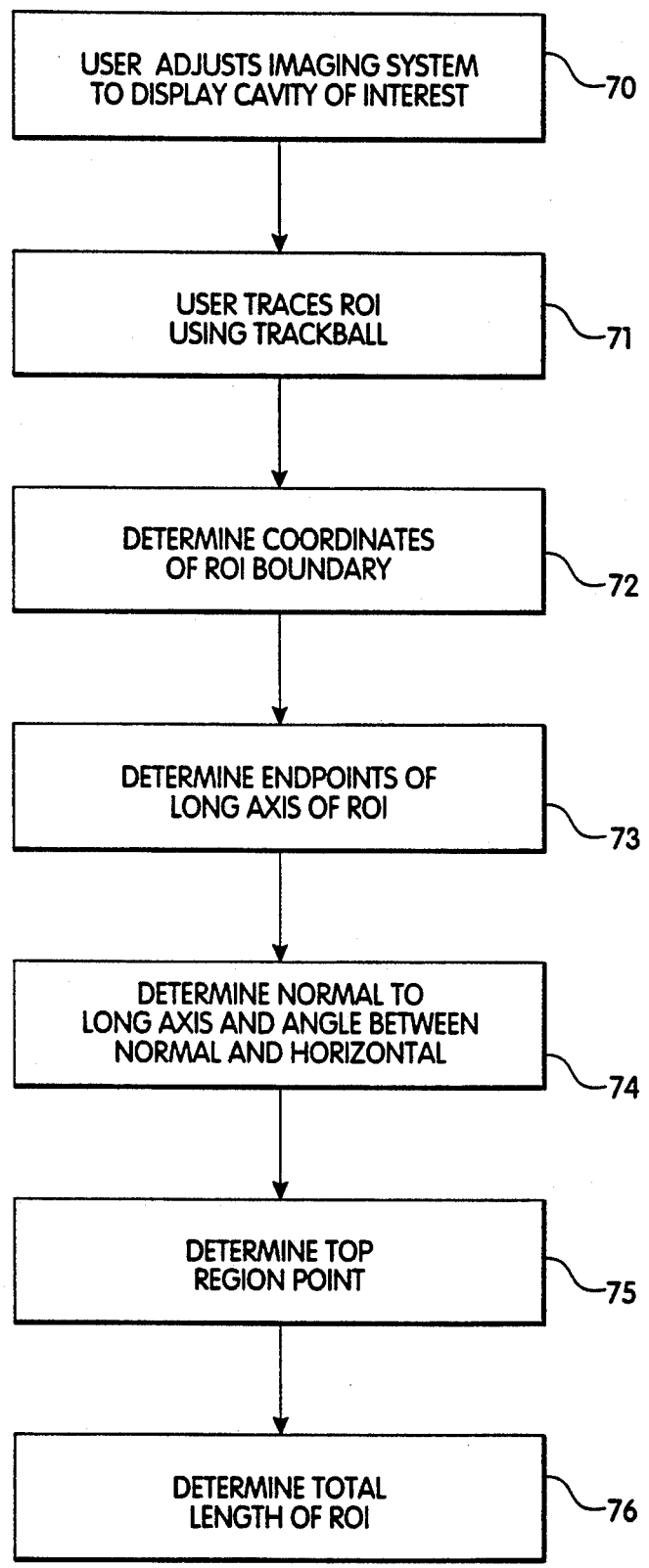
FIG. 3 is a flow diagram which illustrates the steps for determining the parameters of a fixed region of interest in accordance with the invention.

The region of interest used in calculating the volume of a fluid-filled cavity is illustrated in FIGS. 2A and 2B. An image of a human heart 36 at diastole is shown in FIG. 2A, and an image of the heart 36 at systole is shown in FIG. 2B. Assume that it is desired to determine the volume of the left ventricle 38 as a function of time. The left ventricle 38 has its largest volume at diastole, as shown in FIG. 2A, and its smallest volume at systole, as shown in FIG. 2B. The region of interest and associated parameters are determined in accordance with the flow diagram of FIG. 3. The user first adjusts the system such that the left ventricle 38 is clearly shown in the ultrasound image (step 70). The adjustment effectively varies the gain of the scanner signal from scanner 10. When the system is properly adjusted, the blood 37 within the left ventricle 38 is clearly differentiated from the surrounding tissue 39 on the ultrasound image. The proper view of the heart 36 for performing the volume determination method of the present invention is either the apical 4 or apical 2 chamber view. The apical 4 view is an ultrasound cardiac view as scanned through the cardiac apex and showing all four chambers of the heart. The apical 2 view is an ultrasound cardiac view as scanned through the cardiac apex and showing the left ventricle and left atrium.

The user then traces a region of interest 40 around the left ventricle 38 using the trackball 18 to control the location of a marker 41 that is superimposed on the ultrasound display (step 71). The user traces the region of interest 40 beginning at a point 42 on one side of the mitral valve annulus and using the trackball 18 to move the marker 41 up and around the left ventricle 38 to a point 44 on the other side of the mitral valve annulus. An outline of the region of interest 40 is superimposed on the ultrasound image. The user then confirms the region of interest 40, typically by pressing an "approve" or "enter" key on the operator interface 16. The system then determines a long axis 46 as described below.

For accurate determination of the volume of left ventricle 38, the region of interest 40 must surround the image of the blood-filled cavity in left ventricle 38 at the largest volume for which the volume is to be determined. The region of interest 40 does not require precise tracing of the cavity in left ventricle 38. However, the region of interest 40 should not enclose all or part of any blood-filled cavities other than the one being measured.

A preferred technique for tracing the region of interest 40 is described above. However, other techniques for defining the region of interest can be utilized within the scope of the present invention. For example, the region of interest can be determined automatically by the system within the scope of the present invention. Furthermore, a mouse or other cursor control device can be utilized to trace the region of interest 40. It is only required that a region of interest that encloses the body cavity of interest be defined.

The x, y coordinates of the path followed by the marker 41 in tracing the region of interest 40 define the region of interest (step 72). In addition, it is necessary to determine the endpoints of the long axis 46 of the region of interest 40 (step 73). The long axis 46 is defined by its upper endpoint 48 and its lower endpoint 50. When the region of interest 40 is traced from point 42 to point 44, the system joins the ends of the trace between points 42 and 44 by straight line 52. The midpoint of the line 52 is the lower endpoint 50 of axis 46. The upper endpoint 48 is the trace point in the region of interest that is farthest from lower endpoint 50.

Automatic determination of long axis 46 by the system is described above. Alternatively, the user may override the automatic long axis feature and define the long axis 46 manually. The trackball 18 or other cursor control device is used to indicate two points which define long axis 46. The long axis 46 should be positioned as closely as possible to the axis of circular symmetry of the body cavity being measured.

Next, a normal axis 60 to long axis 46 is defined, and the angle between the normal axis 60 and the horizontal axis (the X axis of the display screen) is determined (step 74). Then, the points in the set of region of interest trace points which define the top boundary of the uppermost segment and the points which define the bottom boundary of the lowermost segment are determined. The top region point, which is defined as the intersection of the long axis with the top of the first segment, is determined in step 75.

From the top and bottom segment information and the angle between the normal and the X axis, the total length of the region of interest 40 is determined (step 76). The total length may be different from the length of the long axis 46 because the long axis 46 may not coincide with the longest dimension of the region of interest 40. For example, the line 52 at the lower end of the region of interest 40 may be inclined with respect to long axis 46. The total length is determined by establishing the length along axis 46 for which the normal axis 60 intersects any part of the region of interest 40.

The determination of the region of interest parameters as described above and shown in FIG. 3 is performed by the system controller 22. The region of interest parameters, including the region of interest trace points in polar coordinates, $R_\alpha$, $\beta_\alpha$, the angle between the normal axis 60 and the X axis, the total length of the region of interest and the top region point are supplied by the system controller 22 to the acoustic quantification unit 30. The region of interest parameters are preferably converted to polar coordinates by the system controller 22 and supplied to the acoustic quantification unit 30 in the form of polar coordinates.

Figure 4:
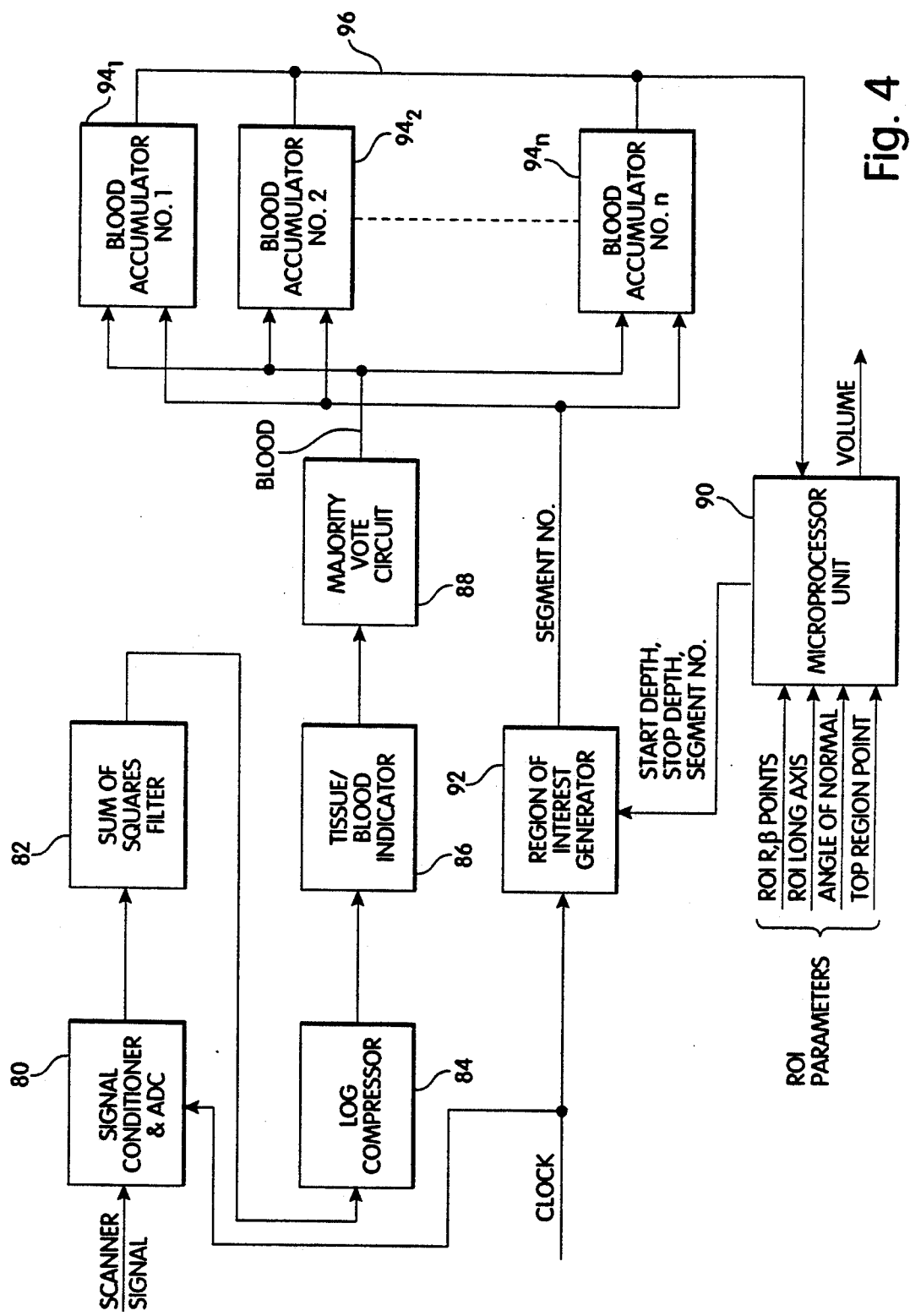
FIG. 4 is a block diagram of an acoustic quantification unit for determining the volume of a fluid-filled cavity in accordance with the invention.

A block diagram of the acoustic quantification unit 30 is shown in FIG. 4. The beamformed scanner signal is applied to a signal conditioner and analog-to-digital converter (ADC) 80 which adjusts the gain of the scanner signal and converts the scanner signal to a series of digital samples. The digital samples from signal conditioner and ADC 80 are applied to a sum of squares filter 82 which squares the signal and integrates the result using a moving window filter. The output of filter 82 is applied to a log compressor 84 which performs a log compression of the form $y = 10 \log x$.

The output of log compressor 84 is input to a tissue/blood indicator 86 which compares the digital samples with a reference level. The scanner signals, and hence the digital samples of the scanner signal, represent the reflected ultrasound energy and are used to generate the ultrasound image. Due to the different characteristics of blood and tissue, the amplitude of ultrasound energy reflected from blood at a given depth is less than the amplitude of ultrasound energy reflected from tissue at the same depth. The reference level is selected between the amplitude representative of blood and the amplitude representative of tissue. The output of tissue/blood indicator 86 has a first state when the input signal is representative of blood and a second state when the input signal is representative of tissue.

The scanner signals contain noise and reflections from different structures, which may cause an erroneous tissue/blood decision. The accuracy of the decision is increased by averaging along each scan line, which is performed by the sum of squares filter 82. The accuracy of the decision is further increased by applying the output of the tissue/blood indicator 86 to a majority vote circuit 88. The majority vote circuit 88 performs an effective averaging by comparing the decisions for each signal sample with decisions for signal samples at the same depth on adjacent scan lines of the ultrasound image. The result is determined by the state of a majority of the samples considered. The majority vote process is preferably performed for a group of samples at the same depth on several successive scan lines, typically three, to provide higher accuracy. The number of samples used to perform a majority vote can be varied depending on the circumstances. The majority vote circuit 88 outputs a signal that is in an active state when the sample is representative of blood and is in an inactive state when the sample is representative of tissue. The use of a majority vote circuit to improve the accuracy of a tissue/blood indicator circuit is described in further detail in application Ser. No. 07/614,780 filed Nov. 9, 1990. The disclosure of application Ser. No. 07/614,780 is hereby incorporated by reference.

Figure 6A:
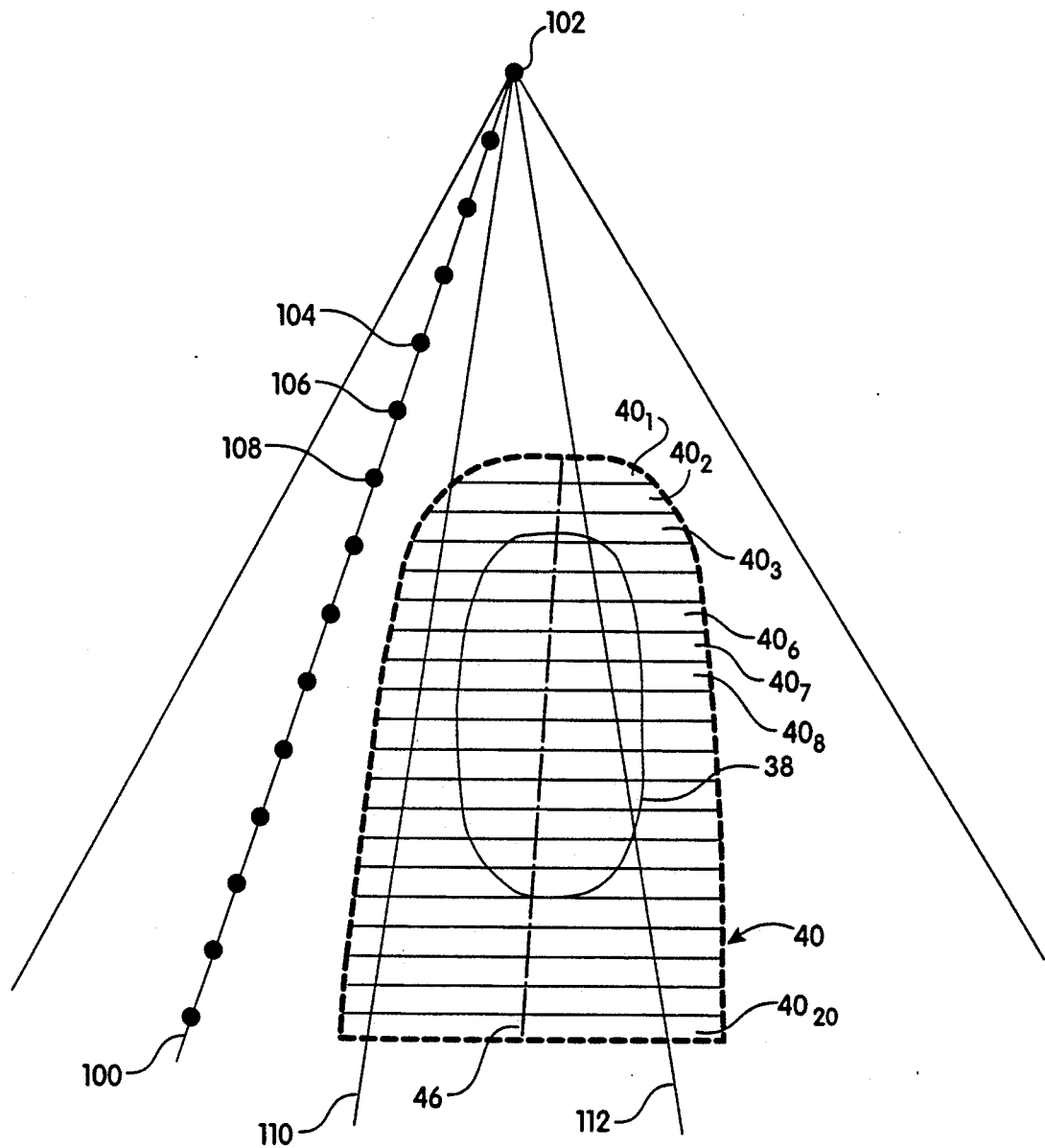
FIG. 6A is a simplified schematic diagram showing an ultrasound image of a blood-filled cavity and a fixed region of interest subdivided into segments.

The sector scan technique for generating an ultrasound image is illustrated in FIG. 6A. The scanner 10 (FIG. 1) transmits an ultrasound pulse along a scan line 100 originating at a point 102, which is typically at the center of the ultrasound transducer. The transmitted ultrasound energy is reflected by various structures within the patient's body. The reflected energy is received by the ultrasound transducer and is converted to electrical signals by the transducer elements. The electrical signals are beamformed by scanner 10 and are converted to digital samples by signal conditioner and ADC 80 (FIG. 4). The digital samples represent the reflected ultrasound energy at points 104, 106, 108, etc. along scan line 100. The samples as a function of time represent successively greater depths along scan line 100. The samples along scan line 100 determine the intensity of pixels in the ultrasound image. The process is repeated for multiple scan lines 110, 112, etc. originating at point 102 to form a two-dimensional sector scan image. A typical sector ultrasound image may have 120 to 240 scan lines. Each sample along each scan line represents the intensity of a pixel in the ultrasound image. As indicated above, "pixel" refers to an incremental area of the sector scan ultrasound image. Each pixel has a truncated annular shape. Because of the sector scan geometry, the areas of the pixels increase linearly with the depth along each scan line. Referring again to FIG. 4, the tissue/blood indicator 86 and the majority vote circuit 88 produce an output for each pixel in the ultrasound image. The output indicates whether the pixel is representative of blood or tissue.

As shown in FIG. 6A, the fixed region of interest 40 surrounds the image of left ventricle 38. In accordance with the present invention, the region of interest 40 is subdivided into a predetermined number of parallel segments $40_1, 40_2, \ldots 40_n$. The segments are defined by parallel lines normal to axis 46 and preferably have equal dimensions along axis 46. In a preferred embodiment, the region of interest 40 is divided into twenty segments. As noted above, the region of interest 40 remains fixed during successive ultrasound images. The segments $40_1, 40_2, \ldots 40_n$ of the region of interest 40 also remain fixed during successive ultrasound images. Some of the segments, such as segments $40_6$, $40_7$ and $40_8$, contain portions of the image of left ventricle 38. Other segments, such as segments $40_1$ and $40_2$, do not contain any portion of the image of left ventricle 38. The number of segments containing portions of the image of left ventricle 38 may vary as a function of time due to the expansion and contraction of the left ventricle.

During scanning, each scan line that passes through the region of interest 40 successively passes through different segments. Thus, the ultrasound energy directed along scan line 112 successively passes through segments $40_1, 40_2, \ldots 40_n$ upon transmission and passes through the same segments in reverse order upon reflection. As described below, the blood area within each segment, which corresponds to area of left ventricle 38 within each segment, is measured along each scan line. The blood areas are accumulated for each segment of the region of interest on successive scan lines. The blood area within each segment is used to calculate the volume of the left ventricle 38 as described below.

Figure 7A:
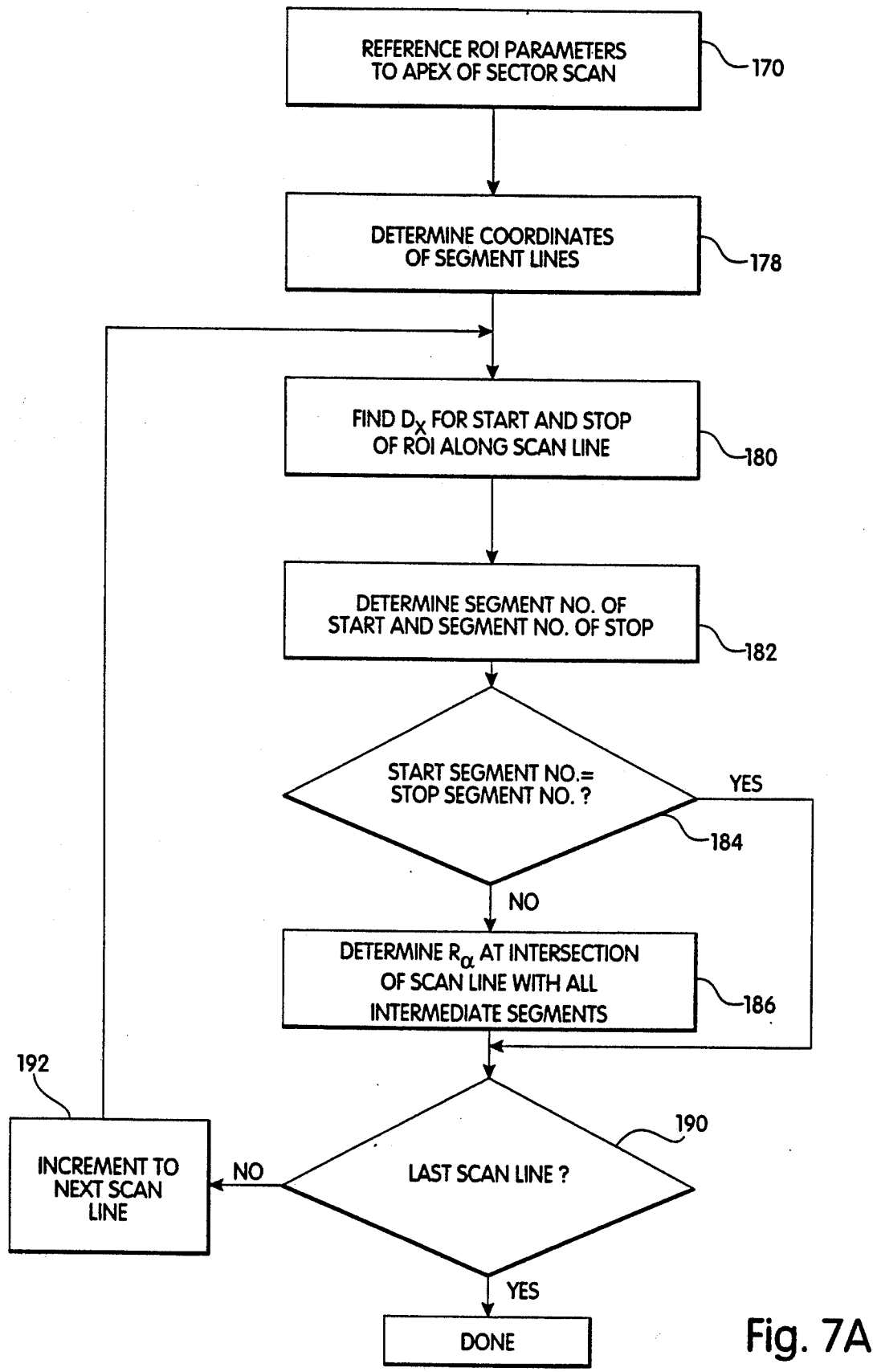
FIG. 7A is a flow diagram which illustrates the steps for calculation of the start and stop depths for each segment of the region of interest along each scan line of the ultrasound image.

Referring again to FIG. 4, the acoustic quantification unit 30 includes a microprocessor unit 90, which may comprise a microprocessor and a local memory. The microprocessor unit 90 receives the region of interest parameters discussed above from the system controller 22 (FIG. 1). The region of interest parameters define the region of interest 40. The microprocessor unit 90 defines the segments $40_1, 40_2 \ldots 40_n$ of the region of interest 40, as shown in FIGS. 6A and 7A. Then the microprocessor calculates a start depth, a stop depth and a segment number for each segment along each scan line in the ultrasound image as described below.

Figure 6B:
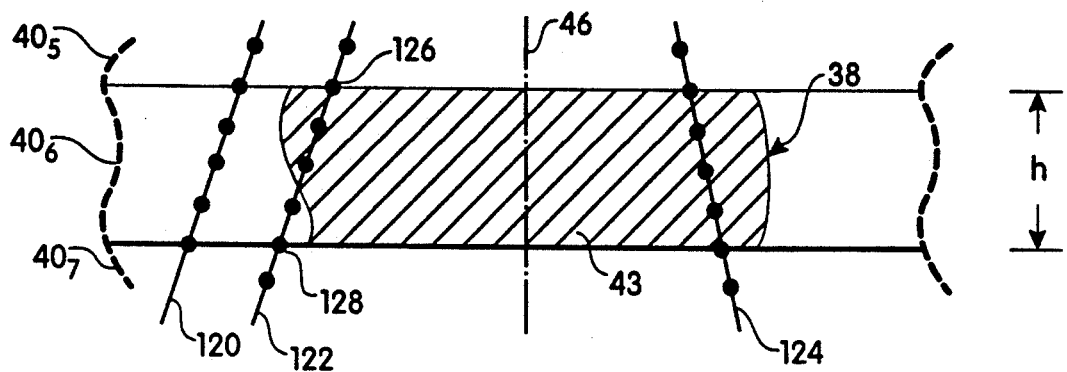
FIG. 6B is a an enlarged view of one of the segments of the region of interest, showing scanning of the segment.

The start depth and the stop depth for a segment of the region of interest are illustrated with reference to FIG. 6B. Segment $40_6$ of region of interest 40 contains a portion 43 of the image of left ventricle 38. Multiple scan lines 120, 122, 124, etc. pass through segment $40_6$ during scanning of an ultrasound image. A start depth 126 along scan line 122 indicates the depth at which the ultrasound energy enters segment $40_6$ for this scan line. A stop depth 128 along scan line 122 indicates the depth at which the ultrasound energy leaves segment $40_6$ and enters segment $40_7$. Thus, samples between start depth 126 and stop depth 128 originate from segment $40_6$. A start depth and a stop depth are established for each scan line that passes through segment $40_6$. In the same fashion, start depths and stop depths are established for all of the other segments of the region of interest. In the example of FIG. 6B, the stop depth of one segment, such as segment $40_5$, is the same as the start depth of the next segment, such as segment $40_6$. However, both parameters are required because, in the general case, the scan line may pass outside the region of interest when it leaves a segment, rather than entering the next segment. Thus, for each scan line, the start depth, the stop depth and segment number are determined for each segment that intersects the scan line.

Referring again to FIG. 4, the start depth, stop depth and segment number information is supplied to a region of interest generator 92. As described below, the region of interest generator 92 outputs a series of segment numbers as each scan line in the ultrasound image is received. The segment number at each instant of time is synchronized to indicate the segment of the region of interest 40 from which the corresponding scanner signal is received. Thus, with reference to FIG. 6A, the region of interest generator 92 may successively output segments $40_1$ through $40_{20}$ along scan line 112. When the scanner signal is received from a portion of the patient's body outside the region of interest 40, the region of interest generator 92 indicates that none of the segments are being scanned.

Figure 5:
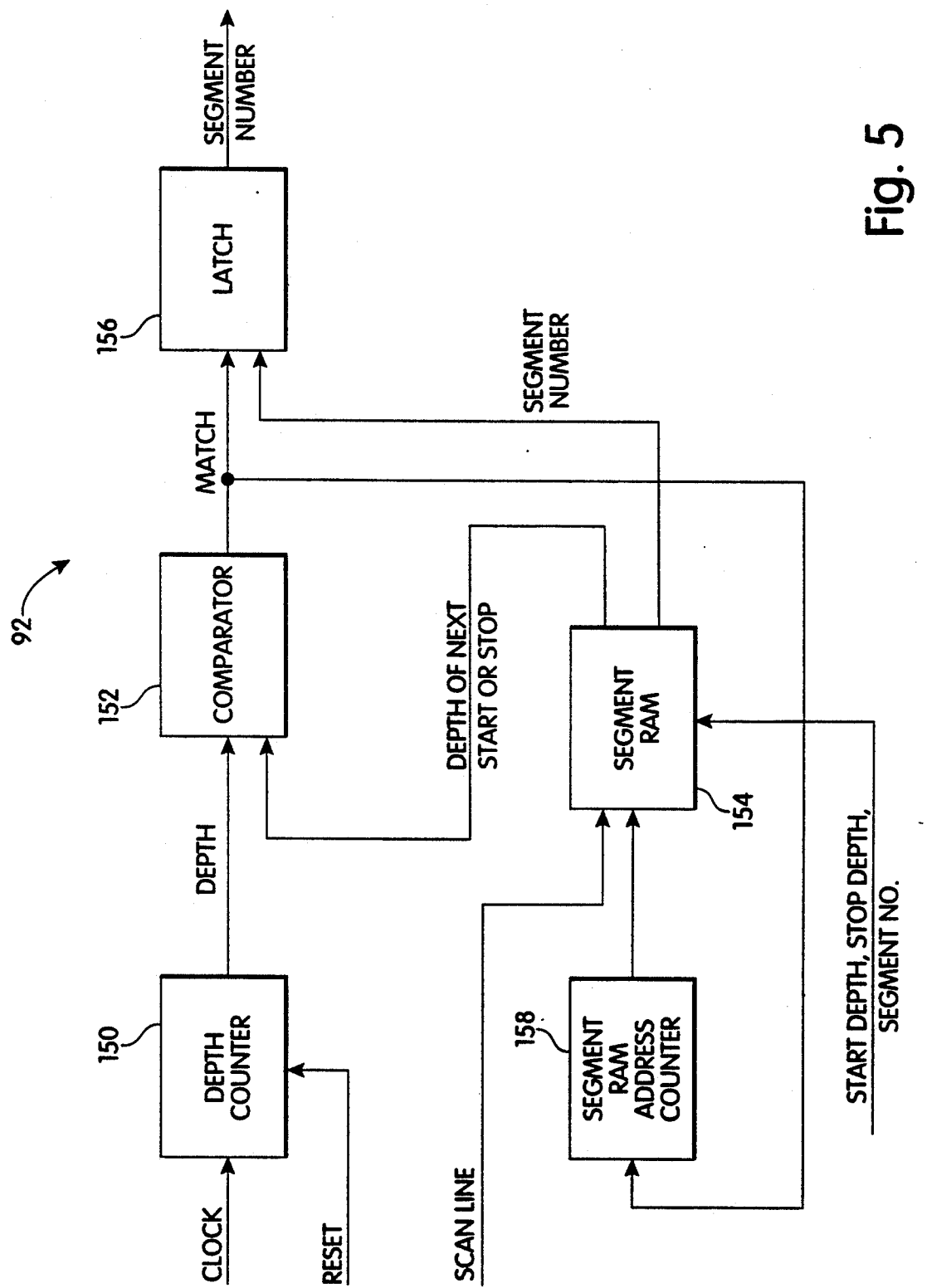
FIG. 5 is a block diagram of the region of interest generator shown in FIG. 4.

A block diagram of the region of interest generator 92 is shown in FIG. 5. A depth counter 150 is incremented by a clock signal from system controller 22. The clock signal is synchronized to the scanner signal from scanner 10. The depth counter 150 is reset prior to each scan line of the ultrasound image. The clock signal clocks both the analog-to-digital converter in signal conditioner and ADC 80 (FIG. 4) and increments the depth counter 150. Thus, the signal conditioner and ADC 80 provides a signal sample for each clock pulse, corresponding to each pixel along a scan line, and the depth counter 150 is incremented by each clock pulse. The value in depth counter 150 represents the depth along a given scan line from which the corresponding sample is received. The output of depth counter 150 is supplied to a comparator 152.

The region of interest generator 92 further includes a segment RAM 154 which stores the start depth, stop depth and segment number information for each scan line as described above. Prior to volume measurement, the start depth, stop depth and segment number information for each segment along each scan line is stored in segment RAM 154. The segment RAM 154 supplies a digital value corresponding to the depth of the next start or stop along the current scan line to the comparator 152. The segment RAM 154 also supplies the current segment number to a latch 156. The segment RAM 154 is addressed by a scan line signal which identifies the current scan line and by a segment RAM address counter 158. The segment RAM address counter 158 is incremented upon each transition between segments or by transitions into or out of the region of interest. Thus, the address supplied to segment RAM 154 represents the current scan line and the segment of the region of interest that is being scanned.

The comparator 152 compares the depth along the current scan line, as supplied by depth counter 150, with the depth of the next start or stop, supplied by segment RAM 154. When a match is detected, a transition between segments or a transition into or out of the region of interest is indicated. The match signal causes the segment number of the next segment, as supplied by the segment RAM 154, to be loaded into latch 156. The output of latch 156 is a segment number which represents the segment of the region of interest currently being scanned. The segment number enables one of the blood accumulators for accumulation of blood area information as described below. When an area outside the region of interest 40 is being scanned, the latch 156 supplies a segment number code which does not enable any of the blood accumulators. Thus, the blood area measurement is performed only within the region of interest on a segment-by-segment basis and is inhibited outside the region of interest.

As shown in FIG. 4, the blood signal from majority vote circuit 88 and the segment number from region of interest generator 92 are input to blood accumulators $94_1$, $94_2$, ... $94_n$. The blood accumulators accumulate the blood area within each respective segment of the region of interest. Thus, for example, blood accumulator $94_1$ accumulates the blood area within segment $40_1$ (FIG. 6A) during successive scan lines of a single ultrasound image. Similarly, blood accumulator $94_2$ accumulates the blood area within segment $40_2$ during the scan lines of a single ultrasound image. The appropriate blood accumulator is enabled by the segment number output of the region of interest generator 92. As noted above, each sample of the received ultrasound signal represents a pixel (as defined above) in the sector scan ultrasound image. Values are accumulated in blood accumulators $94_1$, $94_2$, ... $94_n$ only when the received sample is representative of blood and when the respective segment of the region of interest is being scanned. Thus, the values in each of the blood accumulators represent the blood area within each segment of the region of interest 40. Since the areas of the pixels in a sector scan ultrasound image increase linearly with depth, the areas stored in the accumulators for each pixel increase linearly with depth.

The operation of the blood accumulators can be understood with reference to FIG. 6B. Scan line 120 passes through segment $40_6$ but is outside the portion 43 of left ventricle 38 within segment $40_6$. Thus, during scanning of segment $40_6$ along scan line 120, the majority vote circuit 88 outputs a signal representative of tissue, the region of interest generator 92 outputs segment number $40_6$ and no blood area is stored in accumulator $94_6$. During scanning along scan line 122, the majority vote circuit 88 outputs a signal indicative of blood for the first three pixels and a signal representative of tissue for the fourth pixel. The areas of the first three pixels of segment $40_6$ are stored in blood accumulator $94_6$. During scanning along scan line 124, the majority vote circuit 88 indicates blood in four pixels of segment $40_6$, and the corresponding areas are stored in blood accumulator $94_6$.

Figure 7B:
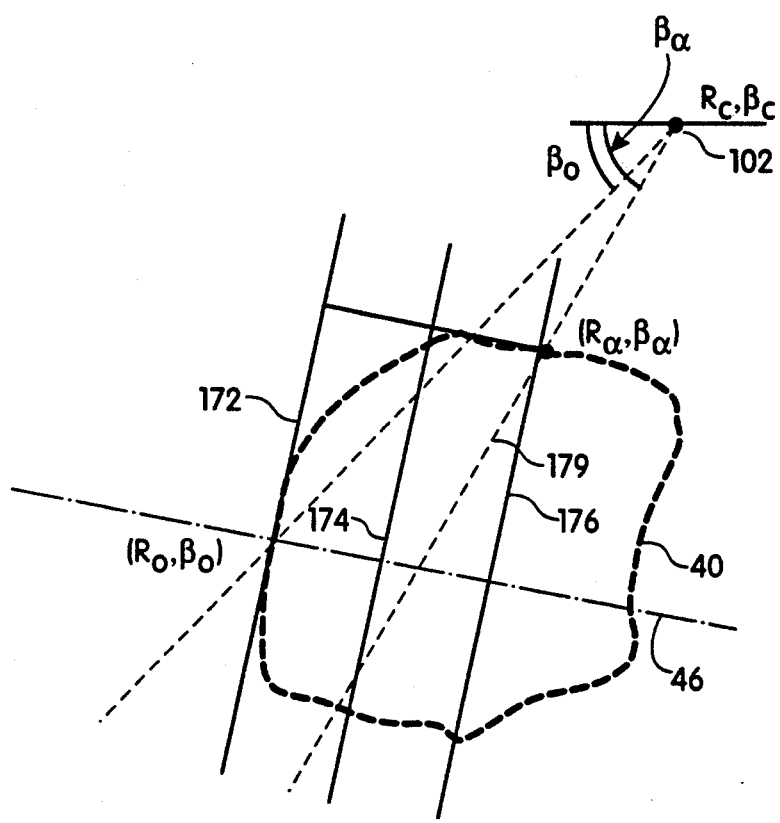
FIG. 7B is a schematic diagram which illustrates the parameters associated with determining the start and stop depths for each segment of the region of interest along each scan line of the ultrasound image.

The steps involved in defining the segments of the region of interest and in determining the start depth and stop depth for each segment along each scan line are described with reference to FIGS. 7A and 7B. The parameters associated with the segments of the region of interest and the start and stop depths are illustrated in FIG. 7B. The microprocessor unit 90 (FIG. 4) receives the polar coordinates of the region of interest 40 along each scan line, thus defining a start depth and a stop depth for each scan line. The microprocessor unit 90 also receives the top region point $R_0$, $\beta_0$ which defines the intersection of the long axis 46 with the top of the first segment of the region of interest 40. The microprocessor unit 90 also receives the slope $k_0$ of the normal to the long axis 46 of the region of interest. Finally, the microprocessor unit 90 receives the total length of the region of interest. The parameters of the region of interest are referenced to the apex of the sector scan, which is defined by point $R_c$, $\beta_c$, in step 170. The top region point $R_0$, $\beta_0$ and the slope $k_0$ of the normal define a segment line 172, which establishes a first segment of the region of interest. In the case where the region of interest is divided into 20 segments, the total length of the region of interest is divided by 20, thereby defining the spacing between segment lines 172, 174, 176, etc. Thus, the region of interest 40 is divided into 20 segments by equally spaced segment lines 172, 174, 176, etc. starting at top region point $R_0$, $\beta_0$ and having a slope $k_0$ (step 178).

Next, the start and stop depths for each segment are determined along a specified scan line. The overall start depth and stop depth of the region of interest 40 are given by the coordinates of the region of interest along that scan line. A distance $D_\alpha$ is defined as the distance, perpendicular to segment line 172, between line 172 and a point $R_\alpha$, $\beta_\alpha$ on a scan line 179. The distance $D_\alpha$ is used to determine the segment number of the overall start depth and stop depth. The value of $D_\alpha$ is determined for the start depth of the region of interest 40 and the stop depth of the region of interest along the scan line 179 in step 180.

From the value of $D_\alpha$, the segment number is determined for the start depth and the stop depth. For example, assume that the region of interest 40 has a total length of 20 units. If the value of $D_\alpha$ for the start depth is 2.5, the start depth is determined to be in segment 3, since segment 3 has values of $D_\alpha$ between 2 and 3. In this way, the segment numbers of the start depth and the stop depth of the region of interest 40 are determined in step 182.

Next, it is determined in step 184 whether the segment number of the start depth is the same as the segment number of the stop depth. This corresponds to the scan line 179 passing through only one segment of the region of interest 40. In this case, no further calculation is required. When the segment number of the start depth and the segment number of the stop depth are not equal, it is necessary to determine the intersections of the scan line 179 with all intermediate segments in step 186. The intersections of the scan line with intermediate segments are determined in accordance with the following equation:

$$D_\alpha = R_\alpha \sin(\gamma_0 + \beta_4) - R_0 \sin(\gamma_0 + \beta_0) \quad (1)$$

where $R_\alpha$ is the distance between apex $R_c$, $\beta_c$ and the intersection point, $\beta_\alpha$ is the angle of the scan line, $R_0$ and $\beta_0$ are the polar coordinates corresponding to point $x_0$, $y_0$ and $\gamma_0$ is defined by $k_0 = \tan \gamma_0$. The value of $R_\alpha$ is the desired start or stop depth. The value of $R_\alpha$ is determined for the intersection of the scan line 179 with each intermediate segment in region of interest 40 in step 186. This is done by solving Equation (1) for $R_\alpha$ and inputting successive values of $D_\alpha$. Since all the quantities in Equation (1) are known, the values of $R_\alpha$ can be calculated. For example, start at $D_\alpha = 3.5$ in region 4 and stop at $D_\alpha = 6.7$ in region 7. Then, find $R_\alpha$ for $D_\alpha = 4$, $D_\alpha = 5$ and $D_\alpha = 6$.

Next, it is determined in step 190 whether the start and stop depths for all scan lines have been completed. When all scan lines have not been completed, the microprocessor unit 90 increments to the next scan line in step 192, and the process of determining the start and stop depths for each segment are repeated. This process is continued until the start and stop depths are determined for all scan lines in the ultrasound image.

Figure 8:
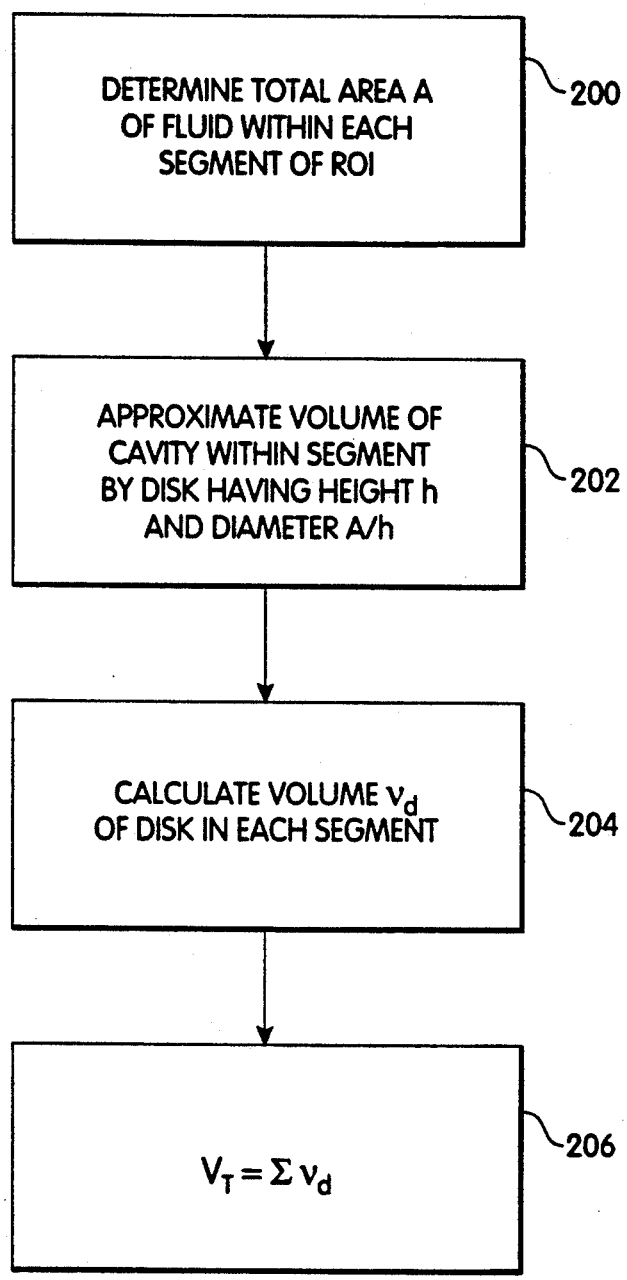
FIG. 8 is a flow diagram which illustrates the steps for calculation of the volume of the fluid-filled cavity.

The steps involved in determining the volume of which represent the blood areas $A_1, A_2 \ldots A_n$ the left ventricle 38 are shown in FIG. 8. After completion of an ultrasound image, the blood accumulators $94_1, 94_2, \ldots 94_n$ contain values which represent the blood areas $A_1, A_2 \ldots A_n$ within the respective segments of region of interest 40 (step 200). The blood areas correspond to the cross-sectional areas of the portion of left ventricle 38 within each segment.

Figure 6C:
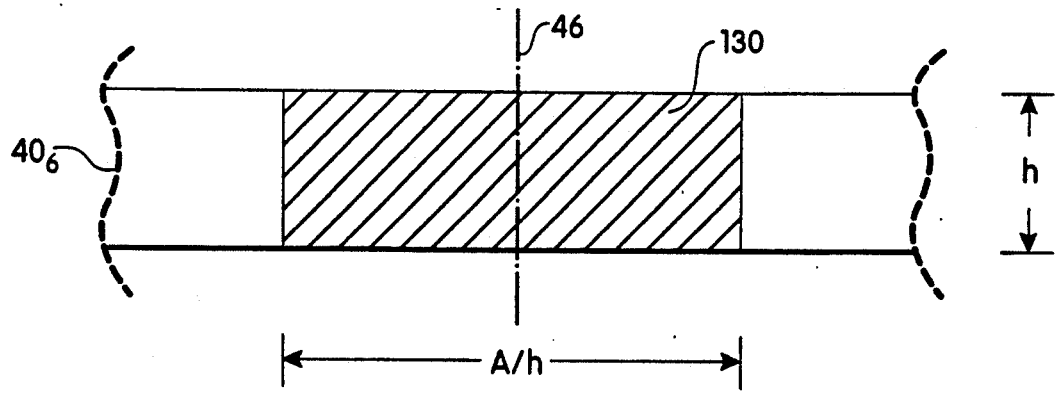
FIG. 6C is an enlarged view of the segment of FIG. 6B, showing approximation of the blood area by a disk.

The blood areas $A_1, A_2 \ldots A_n$ within each of the segments of the region of interest 40 stored in the respective blood accumulators $94_1, 94_2, \ldots 94_n$ are used to calculate the volume of the left ventricle 38 as follows. As shown in FIG. 6B, each segment of the region of interest 40 has a height h along axis 46. The portion 43 of the left ventricle 38 within each segment of the region of interest has an irregular shape, as shown in FIG. 6B. However, the volume of left ventricle 38 within each segment can be approximated by a disk, based on the measured blood area A for each segment. As shown in FIG. 6C, the volume of left ventricle 38 within segment $40_6$ can be approximated by a disk 130 having a height h equal to the height h of the segment $40_6$ and a diameter equal to the measured blood area A within segment $40_6$ divided by the height h (step 202). The volume of the disk 130 is calculated according to the formula $V = \pi A^2/4h$ (step 204). The total volume of the left ventricle 38 is calculated by summing the volumes of the disks within the segments of the region of interest (step 206).

Calculation of the volume of the left ventricle is performed by the microprocessor unit 90 (FIG. 4). The measured blood areas $A_1, A_2 \ldots A_n$ in the respective segments are supplied on a data bus 96 from the blood accumulators $94_1, 94_2, \ldots 94_n$ to the microprocessor unit 90. Microprocessor unit 90 then calculates the left ventricle volume as described above and as illustrated in FIG. 8.

The process described above determines the volume of the left ventricle 38 as indicated on a single ultrasound image of the ultrasound display. As noted above, the region of interest 40 and the segments of the region of interest remain fixed after they are established by the user for a particular volume measurement. Thus, the start depth, stop depth and segment number utilized by the region of interest generator 92 remain fixed. Accordingly, the process described above for determining the volume of left ventricle 38 is repeated for successive images of the ultrasound display to provide a real time measurement of left ventricle volume. That is, during each frame, or image, of the ultrasound display, the blood accumulators $94_1, 94_2, \ldots 94_n$ accumulate blood areas $A_1, A_2, \ldots A_n$ for the respective segments and the microprocessor unit 90 calculates the total volume of the left ventricle from these values. Although the frame rate of the ultrasound display is dependent on the depth being imaged, typical frame rates are on the order of about 20 to 35 frames per second. Thus, the volume of the left ventricle is being measured on a real time basis at a sampling rate equal to the frame rate of the ultrasound display.

The calculated volume can be supplied to the physiological data display 20 (FIG. 1) to provide a numerical display of left ventricle volume as a function of time or a waveform representative of left ventricle volume as a function of time. Furthermore, the calculated volumes can be stored and used for a variety of calculations that may be of interest to the cardiologist. Examples include the rate of change of the volume (dV/dt), the maximum volume, the minimum volume, the difference between the maximum and minimum volumes (stroke volume), and the ejection fraction, which is the normalized stroke volume (maximum volume minus minimum volume divided by maximum volume). Parameters based on the rate of change of volume, dV/dt, including peak filling rate (PFR), peak ejection rate (PER) and time to peak filling rate (TPFR), can also be calculated.

The technique for determining volume in accordance with the present invention has been shown and described above in connection with determining the volume of a left ventricle. It will be understood that the technique can be applied to any cavity or other region in the human body that provides sufficient contrast between the region and the surrounding tissue in an ultrasound display. Furthermore, the technique is not limited to a sector scan display, but can be utilized with a parallel scan ultrasound imaging system. Thus, the technique can be used in linear scanners and curved linear scanners. As described above, the technique of the invention is not limited to phased array scanners.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for determining the volume of a fluid-filled cavity in a patient's body in real time, comprising the steps of:
   a) obtaining a real time, two-dimensional ultrasound display of a fluid-filled cavity and the surrounding tissue, said ultrasound display comprising a sequence of ultrasound images on a display screen;
   b) determining parameters of a fixed, user-defined region of interest surrounding the ultrasound display of the cavity at the largest volume for which said volume determination is to be made;
   c) subdividing said region of interest into a predetermined number of segments which entirely fill said region of interest, each of said segments having a height;
   d) classifying each pixel, at least within said region of interest, of an ultrasound image in said sequence of ultrasound images as a fluid pixel which represents fluid or a tissue pixel which represents tissue;
   e) determining an area of fluid pixels within each segment of said region of interest;
   f) calculating the volume of said cavity from the area of fluid pixels within each segment of said region of interest; and
   g) repeating steps d) through f) for each ultrasound image of said sequence of ultrasound images to provide the volume of said cavity at each of the times when said ultrasound images were obtained.

2. A method as defined in claim 1 wherein said cavity comprises a ventricle of the human heart and said fluid comprises blood.

3. A method as defined in claim 1 wherein the step of calculating the volume of said cavity comprises the steps of approximating a volume of said cavity within each segment by a disk having a height equal to the height of said segment and a diameter equal to the total area of said fluid pixels dividing by the height, calculating the volume of the disk in each segment of said region of interest, and summing the volumes of the disks in the segments of said region of interest to provide the volume of said cavity.

4. A method as defined in claim 1 wherein the step of determining parameters of said fixed region of interest includes defining a long axis of said region of interest and wherein the height of each segment of said region of interest is defined along said along axis.

5. A method as defined in claim 1 wherein the step of determining parameters of said region of interest includes determining the coordinates of a boundary of said region of interest, determining a long axis of said region of interest and determining an angle between a normal to said long axis and a horizontal axis of said display screen, and wherein the step of subdividing said region of interest includes subdividing said region of interest by spaced lines normal to the long axis.

6. A method as defined in claim 5 wherein the step of subdividing said region of interest includes subdividing said region of interest into 20 segments having parallel boundaries normal to said long axis.

7. A method as defined in claim 6 wherein said segments have equal heights along said long axis.

8. A method as defined in claim 1 wherein the step of obtaining an ultrasound display includes transmitting and receiving ultrasound energy along a plurality of scan lines and wherein the step of determining the total area of fluid pixels includes accumulating areas of fluid pixels within each segment along each scan line to provide the total area of fluid pixels within each segment.

9. A method as defined in claim 8 wherein the step of determining the area of fluid pixels with each segment of said region of interest further includes the steps of storing a start depth, a stop depth and a segment number for each segment along each scan line, and storing the area of fluid pixels within each segment in an accumulator corresponding to said segment number when a depth along each scan line between said start depth and said stop depth is being scanned.

10. Apparatus for determining the volume of a fluid-filled cavity in a patient's body in real time comprising:
    means for obtaining a real time, two-dimensional ultrasound display of a fluid-filled cavity and the surrounding tissue, said ultrasound display comprising a sequence of ultrasound images on a display screen;
    means for determining parameters of a fixed, user-defined region of interest surrounding the ultrasound display of the cavity at the largest volume for which said volume determination is to be made;
    means for subdividing said region of interest into a predetermined number of segments which entirely fill said region of interest, each of said segments having a height; and
    means for processing each ultrasound image of said sequence of said ultrasound images to provide the volume of said cavity at each of the times when said ultrasound images were obtained, said means for processing comprising:
    means for classifying each pixel, at least within said region of interest, of an ultrasound image in said sequence of ultrasound images as a fluid pixel which represents fluid or a tissue pixel which represents tissue;
    means for determining an area of fluid pixels within each segment of said region of interest, and
    means for calculating the volume of said cavity from the area of fluid pixels within each segment of said region of interest.

11. Apparatus as defined in claim 10 wherein said means for determining parameters of said fixed region of interest includes means for determining the coordinates of a boundary of said region of interest, means for determining a long axis of said region of interest and means for determining an angle between a normal to said long axis and a horizontal axis of said display screen and wherein said means for subdividing said region of interest includes means for subdividing said region of interest by spaced lines normal to the long axis.

12. Apparatus as defined in claim 10 wherein said means for obtaining an ultrasound display includes means for transmitting and receiving ultrasound energy along a plurality of scan lines and wherein said means for determining the area of fluid pixels includes means for accumulating areas of fluid pixels within each segment along each scan line to provide the area of fluid pixels within each segment.

13. Apparatus as defined in claim 12 wherein said means for determining the total area of said fluid pixels further includes means for storing a start depth, a stop depth and a segment number for each segment along each scan line and means for storing the area of fluid pixels within each segment in an accumulator corresponding to said segment number when a depth along each scan line between said start depth and said stop depth is being scanned.

14. Apparatus as defined in claim 10 wherein said means for calculating the volume of said cavity comprises:

means for approximating the volume of said cavity within each segment of said region of interest by a disk having a height equal to the height of said segment and a diameter equal to the area of said fluid pixels within each segment divided by the height;

means for calculating the volume of the disk in each segment of said region of interest; and means for summing the volumes of the disks in the segments of said region of interest to provide the volume of said cavity.

* * * * *